United States Patent
Staples et al.

(10) Patent No.: US 8,795,649 B2
(45) Date of Patent: Aug. 5, 2014

(54) NITRITE SALTS AS POISONS IN BAITS FOR OMNIVORES

(75) Inventors: Linton Drew Staples, Canterbury (AU); Steven Lapidge, South Australia (AU); Brendan Cowled, Australian Capital Territory (AU); Simon Humphrys, South Australia (AU)

(73) Assignee: Invasive Animals Ltd., Canberra (AU)

( * ) Notice: Subject to any disclaimer, the term of this patent is extended or adjusted under 35 U.S.C. 154(b) by 531 days.

(21) Appl. No.: 12/449,806

(22) PCT Filed: Feb. 28, 2008

(86) PCT No.: PCT/AU2008/000260
§ 371 (c)(1),
(2), (4) Date: Mar. 1, 2010

(87) PCT Pub. No.: WO2008/104028
PCT Pub. Date: Sep. 4, 2008

(65) Prior Publication Data
US 2010/0150978 A1    Jun. 17, 2010

Related U.S. Application Data

(60) Provisional application No. 60/903,891, filed on Feb. 28, 2007.

(30) Foreign Application Priority Data

Feb. 28, 2007 (AU) ................................. 2007901050

(51) Int. Cl.
*A01N 25/00* (2006.01)
*A23K 1/17* (2006.01)
*A23K 1/165* (2006.01)
*C07C 203/00* (2006.01)
*C07C 331/00* (2006.01)
*C07C 381/00* (2006.01)

(52) U.S. Cl.
USPC .............. 424/84; 424/405; 424/442; 558/488

(58) Field of Classification Search
USPC .............................. 424/84, 405, 442; 558/488
See application file for complete search history.

(56) References Cited

U.S. PATENT DOCUMENTS 2,712,997 A   7/1955   Cooley
4,001,445 A   1/1977   Horrocks et al.
(Continued)

FOREIGN PATENT DOCUMENTS

DE        821142        11/1951
WO    WO 99/02035      1/1999
(Continued)

OTHER PUBLICATIONS

Cowled et al., "Attractiveness of a novel omnivore bait, PIGOUT, to feral pigs (*Sus scrofa*) and assessment of risks of bait uptake by non-target species," 2006, Wildlife Research, 33(8)(: 651-660, Abstract.*

(Continued)

*Primary Examiner* — Jane C Oswecki
(74) *Attorney, Agent, or Firm* — Wolf, Greenfield & Sacks, P.C.

(57) ABSTRACT

The present invention relates to baits, especially baits to be used in humane methods for controlling feral omnivore populations. The invention also relates to methods of manufacturing the baits.

11 Claims, 7 Drawing Sheets

(56) References Cited

U.S. PATENT DOCUMENTS

| | | | |
|---|---|---|---|
| 4,144,188 | A | 3/1979 | Sato |
| 4,220,668 | A | 9/1980 | Wistreich et al. |
| 4,234,607 | A | 11/1980 | Ohta et al. |
| 4,263,329 | A | 4/1981 | Olson et al. |
| 4,305,965 | A | 12/1981 | Cheney |
| 4,463,026 | A | 7/1984 | Chandler et al. |
| 4,490,352 | A | 12/1984 | Miller |
| 4,805,340 | A | 2/1989 | Becker et al. |
| 4,874,607 | A | 10/1989 | Hodgson |
| 5,062,237 | A | 11/1991 | Kitagawa et al. |
| 2008/0160058 | A1* | 7/2008 | Staples ......................... 424/410 |
| 2010/0150978 | A1 | 6/2010 | Staples et al. |

FOREIGN PATENT DOCUMENTS

| | | |
|---|---|---|
| WO | WO 99/44622 | 4/2001 |
| WO | WO 2005/068559 | 7/2005 |
| WO | WO 2007145334 | 12/2007 |

OTHER PUBLICATIONS

London et al., "An attempt to produce chronic nitrite toxicosis in swine," 1967, J. Amer. Veterinary Med. Assn., 150(4): 398-402, Abstract.*

Smith et al., "Incorporation of zinc phosphide rodenticide into integrated management of rats in sugarcane crops," 2002, Sugarcane International, pp. 3-8, Abstract.*

Wasserman et al., "The Effect of Sodium Nitrite on the Flavor of Frankfurters," 1972, J. of Food Science, vol. 37, pp. 536-538.*

London et al., "An Attempt to Produce Chronic Nitrite Toxicosis in Swine," 1967, J. of the American Veterinary Medical Assn., 150(4): 398-402.*

Cowled et al., "Attractiveness of a novel omnivore bait, PIGOUT, to feral pigs (Sus scrofa) and assessment of risks of bait uptake by non-target species," (2006), Wildlife Research, 33(8): 651-660.*

Smith et al., "Incorporation of zinc phosphide rodenticide into integrated management of rats in sugarcane crops," (2002), Sugar Cane International, Sept./Oct. pp. 3-8.*

Wasserman et al., "The Effect of Sodium Nitrite on the Flavor of Frankfurters", 1972, J. of Food Science, 37:536-538.*

Winks et al., "Nitrite Poisoning in Pigs," 1950, The Queensland Journal of Agricultural Science, 7(1&2):1-14.*

Cowled et al., "Attractiveness of a novel omnivore bait, PIGOUT, to feral pigs (Sus scrofa) and assessment of risks of bait uptake by non-target species," 2006, Australian Wildlife Research, 33(8):651-660—Abstract only.*

Smith et al., "Incorporation of zinc phosphide rodenticide into integrated management of rats in sugarcane crops," Sep./Oct. 2002, Sugar Cane International, pp. 3-8.*

ACTA 1080 Concentrate, PIGOUT Label, Jun. 1, 2013; Material Safety Data Sheet, Australian Control Technologies (Australia) Pty Ltd; pp. 1-5.*

International Search Report for related European application No. EP08706142.0 dated Feb. 23, 2012.

Agar and Harley (1972) Experientia 28:1248-49.

Alexiou (1984) Effects of feral pigs (Sscrofa) on sub-alpine vegetation at Smokers Gap, ACT, Proceedings of Ecological Society of Australia, 12: 135-142.

Anonymous. 2004. Summary of requirements for authority to obtain, use or supply schedule 7 poisons. NSW Department of Health, Gladesville, NSW.

Argonne National Laboratory, EVS, "Nitrate and Nitrite" Human Health Fact Sheet, Aug. 2005.

Beasley, "Absorption, Distribution, Metabolism, and Elimination: Differences Among Species", Veterinary Toxicology http://www.ivis.org/advances/Beasley/AppC/ivis.pdf.

Beutler and Mikus, Bloob 18:455-67 (1961).

Board, et al, "Methaemoglobin and Its Reduction in Nucleated Erythrocytes from Reptiles and Birds", Comp. Biochem. Physiol, 1997. vol. 57B, 265-267.

Bodansky, O. (1951) Pharmaceutical Reviews 3:144-91.

Bouchet G. and Bouchet A. 1938. Toxicity of sodium nitrite (translated). Bull. Acad. Vet. Fr. 11: 433-435.

Calabrese, et al, "The effects of Joint Exposures to Environmental Oxidants on Methemoglobin Formation: Copper/Nitrite and Copper/Chrorite", J. Environ. Sci. Health. A27(3), 926-642 (1992).

Campbell, T, Lapidge, S, Long, D, "Using Baits to Deliver Pharmaceuticals to Feral Swine in Southern Texas", Wildlife Society Bulletin, 34(4), 1184-1189.

Carrigan M.J. and Gardner I.A. 1982. Nitrate poisoning in cattle fed sudax (Sorghum sp. Hybrid) hay. The Australian Veterinary Journal. 59: 155-157.

Choquenot, D., McIlroy, J. and Korn, T., (1996) Managing Vertebrate Pests: Feral Pigs (Ed. M. Bomford) Bureau of Resource Sciences, Australian Government Publishing Service, Canberra 163 pp.

Counter D.E., Giles N. and Redmond R. 1975. Stored rainwater as a cause of nitrite poisoning in pigs. Veterinary Record. 96: 412.

Edwards W.C. and McCoy C.P. 1980. Nitrate poisoning in Oklahoma cattle. Veterinary Medicine. 75:457.

Counters, D. E., et al, The Veterinary Record, May 3, 1975, p. 412.

Cowled et al, Australian Wildlife Research 33: 427-437.

Cox and Wendel, (1942) The Journal of Biological Chemistry 331-340.

Crabtree G. Review of current vertebrate pesticides, Proceedings of the $1^{st}$ vertebrate pest conference 1962.

Czarnowski A. and Musielak B. 1973. Observations on the toxicity of nitrates and nitrites for broiler fowl (translation). Medyeyna weterynaryjna. 29 No. 10 617-619.

D. Lewis, "The metabolism of nitrate and nitrite in the sheep. 1. The reduction of nitrate in the rumen of the sheep", Biochem J. Feb. 1951; 48(2): 175-180.

D. Lewis, "The metabolism of nitrate and nitrite in the sheep. 2. Hydrogen Donators in Nitrate Reduction by Rumen Micro-Organisms In Vitro", Biochem J. 1951; 49: 149-153.

Dennis et al, "Nitrates and nitrites" Encyclopedia of Food Sciences and Nutrition, 2003, pp. 4136-4141.

Derwent WPIDS Online Abstract Accession No. 2003-446440 [42] of RU2203559 (Krasolnikov O Yu) May 10, 2003.

Egyed M.N. and Hanji V. 1987. Factors contributing to recent outbreaks of acute nitrate poisoning in farm ruminants. Israel Journal of Veterinary Medcine. 43: 50-55.

Follett et al, "Determination of nitrite and nitrate in meat products", Journal of the Science of Food and Agriculture, 1963, vol. 14, Issue 3, p. 138-144.

Fsanz. No Date. Schedule 1: Permitted uses of food additives by food type, Issue 69. Food standards Australia and New Zealand. Accessed online Dec. 1, 2005 at http://www.foodstandards.gov.au/srefiles/ACF40E7.pdf.

Gibson R. 1975. An outbreak of nitrite poisoning in sows. Veterinary Record. 96: 270.

Gibson. R., The Veterinary Record, Mar. 22, 1975, p. 270.

Guengerich FP, "Comparisons of catalytic selectivity of cytochrome P450 subfamily enzymes from different species", Chem Biol Interact, Oct. 24, 1997; 106(3): 161-82.

Gwatkin R. and Plummer P.J.G. 1946. Toxicity of certain salts of sodium and potassium for swine. Canad. J. comp. Med. 10: 188-190.

Henderson R. Et al, Current practices in sequential use of possum baits Department of Conservation Technical Series 22 (1999) p. 1172-6873.

Hone, J., (2002) Feral pigs in Namadgi National Park: dynamics, impacts and management, Biological Conservation 105: 231-242).

Hvidsten H. 1955. Studies on the effect of nitrite in pig feed. Acta agric. Scand. 5: 245-256.

Jensen C.W. and Anderson H.D. 1941. Rate of formation and disappearance of methemoglobin following oral administration or injection of sodium nitrite. Proc. S. Dak. Acad. Sci. 21: 37-40.

Joint Expert Advisory Committee on Antibiotic Resistance (JETACAR). 1999. The use of antibiotics in food-producing animals: antibiotic-resistant bacteria in animals and humans. Report of the Joint Expert Advisory Committee on Antibiotic Resistance (JETACAR). Commonwealth Department of Health and Aged Care and Commonwealth Department of Agriculture, Fisheries and Forestry. Canberra, Australia.

(56) References Cited

OTHER PUBLICATIONS

Jones, "Poison Nitrate/nitrite", *In Practice*, May 1993, 146-147.
Kovacs J., Balintffy I. and Schink Z. 1960. Aetiology and treatment of methaemoglobinaemia in pigs (translated from Hungarian). *Mag. Allator. Lapja* 15: 216-222.
Kozma A. and Szilagyi M. 1967. Plant, drinking water, and soil examinations in relation to methaemoglobinaemia of swine (translation). *Magy. Allatorv. Lap.* 22: 257-261.
Lacki, M. J., and Lancin, R. A., (1986) Effects of wild pigs on beech growth in Great Smoky Mountains National Park, *Journal of Wildlife Management* 50: 655-659.
Lapidge, S, Dall, D, Hunt, R, Cowled, B, Smith, M, Staples, L, "A Review of the Impact of Sheep Predators in Australia and New Control Methods Under Development".
McIlroy et al, Australian Wildlife Research 16: 195-202.
McParland PJ et al, Nitrite poisoning in pigs, Vet Rec (1980) vol. 106 No. 9 p. 201.
McParland, P. J., et al, The Veterinary Record, Mar. 1, 1980, p. 201.
Miller D.J.S., O'Connor J.J. and Roberts N.L. 1986. Tiamulin/salinomycin interactions in pigs. *Veterinary Record.* 118: 73-75.
Miller, B. and Mullette, K., (1985) Rehabilitation of an endangered Australian bird: the Lord Howe Island Woodhen, *Tricholimnas sybvestris, Biological Conservation*, 34: 55-95.
Mitchell, J. and Mayer, R., (1997) Digging by feral pigs in the wet tropics world heritage area of north Queensland, *Wildlife Research*, 24: 591-601.
Mitchell, J., (2000) Ecology and management of feral pigs in tropical rainforest, Unpublished PhD Thesis, James Cook University of North Queensland, Townsville.
O'Brien and Lukins, Australian Wildlife Research 17: 101-12.
O'Brien et al, Australian Wildlife Research 15: 285-291.
Parkinson, et al, "Comparative Erythrocyte Metabolism in Marsupials and Monotremes".
Pott J.M. and Skov B. 1981. Monnensin-tiamulin interactions in pigs. *Veterinary Record.* Dec. 12 pp. 545.
Ramey C et al, Back to the future for APHIS's vertebrate pesticides, Proceedings of the 15$^{th}$ vertebrate pest conference 1992.
Robinson W.D. 1942. Mangel poisoning in pigs. *N.Z. Journal of Agriculture.* 65: 199-202.
Rockwood, et al, "Species Comparison of Methemoglobin Reductase", (2003) 228: 79-83.
Shimada, et al, "Cytochrome P450-dependent drug oxidation activities in liver microsomes of varioanimal species including rats, guinea pigs, dogs, monkeys, and humans", *Archives of Toxicology*, vol. 71, No. 6, 401-408.
Singer, F. J., Swank, W. T., and Clebsch, E. E. C., Effects of wild pig rooting in a deciduoforest., *Wildlife Management* 48: 464-473.
Smith & Butler., Am. J. Physiology. 210(2):347-350, 1966.
Smith and Beutler (1966) Methaemoglobin formation and reduction in man and varioanimal species. *Am. J. Physiol.* 210, 347-350.
Van Heugten, "Guidelines for Water Quality in Pigs", *Animal Science Facts*.
Vyt, P et al, Viaams Diergeneeskundig Tijdschrift, 2005, 74, 359-363.
Vyt, P., "Nitrite intoxication in sows" *The Veterinary Record* 158:456 (2006).
Wanntorp H. and Swahn 0, 1953. The toxicity of whey for swine in conjunction with bacterial reduction of nitrate to nitirite. *Proc. XVth Int. vet. Congr. Stockholm. 1953. I, Pt 1.* 496-501.
Whitkamp R.F., Nijmeijer S.M., Csiko G. and Van Miert A.S.J.P.A.M. Tiamulin selectively inhibits oxidative hepatic steroid and drug metabolism in vitro in the pig. *Journal of Veterinary Pharmacological Therapy.* 17: 317-322.
Whittington et al, "Comparative Study of the Antioxidant Defence Systems in the Erythrocytes of Australian Marsupials and Monotremes". Comp Biochem Physiol 10C:267-272, 1995.
Williams, "Inter-Species Variations in the metabolism of Xenobiotics", *Eight Ciba Medal Lecture*, 1973, 359-377.
Winks, W. R., The Queensland Journal of Agricultural Science, vol. 7, No. 1 and 2, Mar. and Jun. 1950, pp. 1-14.
Yong C., Brandow R.A. and Howlet P. An unusual case of nitrate poisoning in cattle. *Canadian Veterinary Journal.* 31: 118-119.
Beasley, "Absorption, Distribution, Metabolism, and Elimination: Differences Among Species", *Veterinary Toxicology* http://www.ivis.org/advances/Beasiey/AppC/ivis.pdf pp. 1-19 (Aug. 9, 1999).
Fsanz. [No Date] Schedule 1: *Permitted uses of food additives by food type, Issue 69*. Food standards Australia and New Zealand. Accessed online Dec. 1, 2005 at http://www.foodstandard.gov.au/_srefiles/ACF40E7.pdf.
Parkinson et al, "Comparative Erythrocyte Metabolism in Marsupials and Monotremes" pp. 1-5 (1995).
Robinson "Mangel poisoning in pigs." *N.Z. Journal of Agriculture.* 65: 199-202 (1942).
Rockwood, et al, "Species Comparison of Methemoglobin Reductase", *Drug Assessment Med. Res. Inst. Of Chem. Defense* (2003) 228: 79-83.
Van Heugten, "Guidelines for Water Quality in Pigs", *Animal Science Facts* pp. 1-4 (2000).

\* cited by examiner

NITRITE SALTS AS POISONS IN BAITS FOR OMNIVORES

FIELD OF THE INVENTION

The present invention relates to baits, especially baits to be used in humane methods for controlling feral omnivore populations. The invention also relates to methods of manufacturing the baits.

BACKGROUND OF THE INVENTION

Globally feral omnivorous animals cause remarkable environmental, biodiversity, agricultural and or industry damage. For example, omnivorous rodents are a global problem requiring vast resources to control. In New Zealand, introduced brush tail possums now number an estimated 60-70 million. The damage they cause is both environmental and financial: they prey on eggs and chicks of native birds and on native insects, damage native forests and spread bovine tuberculosis, posing an immense threat to dairy and beef industries.

In Australia, feral pigs are estimated to number in excess of 4 million with some estimates as high as 25 million. Feral pigs occupy some 40% of the land mass of Australia. These population estimates mean that there may be more feral pigs in Australia than grazed cattle. Feral pigs inhabit, and are well adapted to, a wide range of habitats that include sub-alpine, temperate, sub-tropical, tropical and arid zones, and they are present in most Australian states and territories. While brushtail possum over browsing of native and agriculturally important flora in Tasmania is also of some concern.

Furthermore, in the United States, the presence of some 4 million feral pigs (also referred to as hogs, boar, or swine) has been reported in some 28 states ranging from California to Virginia, the majority residing in Texas. Feral pigs are the most abundant introduced ungulate in the United States.

Feral pigs have a very high fecundity and frequently raise litters in excess of 6 piglets per breeding sow. Thus, the capacity for feral pig populations to respond to control measures or to totally exploit a food supply is large.

Feral pigs adversely impact agricultural production, environments and ecosystems. A number of studies have identified a range of environmental and agricultural problems arising from feral pig infestations (Alexiou (1984) Effects of feral pigs (*Sus scrofa*) on sub-alpine vegetation at Smokers Gap, ACT, Proceedings of Ecological Society of Australia, 12: 135-142; Tisdell, C. A., (1982) Wild Pigs: Environmental Pest or Economic Resource? Pergamon Press, Sydney; Miller, B. and Mullette, K., (1985) Rehabilitation of an endangered Australian bird: the Lord Howe Island Woodhen, *Tricholimnas sybvestris, Biological Conservation,* 34: 55-95; Mitchell, J. and Mayer, R., (1997) Digging by feral pigs in the wet tropics world heritage area of north Queensland, *Wildlife Research,* 24: 591-601; Choquenot, D., McIlroy, J. and Korn, T., (1996) Managing Vertebrate Pests: Feral Pigs (Ed. M. Bomford) Bureau of Resource Sciences, Australian Government Publishing Service, Canberra 163 pp; Mitchell, J., (2000) Ecology and management of feral pigs in tropical rainforest, Unpublished PhD Thesis, James Cook University of North Queensland, Townsville; Hone, J., (2002) Feral pigs in Namadgi National Park: dynamics, impacts and management, *Biological Conservation* 105: 231-242); Singer, F. J., Swank, W. T., and Clebsch, E. E. C., Effects of wild pig rooting in a deciduous forest., *Wildlife Management* 48: 464-473; Lacki, M. J., and Lancin, R. A., (1986) Effects of wild pigs on beech growth in Great Smoky Mountains National Park, *Journal of Wildlife Management* 50: 655-659. The key points from these various studies are summarised below.

The predatory behaviour of feral pigs causes major economic damage for animal production enterprises over wide areas. The damage is so severe that some areas cannot sustain productive grazing due solely to the widespread infestation of feral pigs. The species' impact on agricultural production has been conservatively estimated to be in excess of 100 million Australian dollars annually.

Feral pigs also cause significant damage to the environment due to their destructive foraging habits which include digging (rooting) and consumption of plants. This destructive behaviour can damage infrastructure including fencing, dams and levy banks and also causes damage to wide areas of fragile riparian habitat. Their effect on native animal species is unknown but is likely to be severe in view of their predatory behaviour and competition for food resources.

Apart from direct damage to grazing enterprises and the environment, the biggest risk from feral pigs arise from their capacity to harbour several major human and animal diseases. Many diseases are zoonotic and the pig provides an ideal amplifying host. Japanese encephalitis virus, leptospirosis, brucellosis and melioidosis have already been detected in feral pigs in Australia. However an even greater risk comes if there is an incursion of foot and mouth disease (FMD) virus into the feral pig population, where the cloven hoofed pigs provide an amplifying host and virus carrier that is widely distributed and highly mobile.

In the United States, pseudorabies virus (PRV) has been eradicated from domestic pigs however PRV continues to circulate in feral pig and raccoon populations. Accordingly, feral omnivore populations can also be a reservoir for fresh PRV outbreaks.

Details of the environmental, human health, animal health and agricultural production problems that arise already, or which might arise, from an unchecked expansion in feral pig numbers are provided in the book "*Managing Vertebrate Pests: Feral Pigs*" (Choquenot, D., McIlroy, J. and Korn, T., (1996) Managing Vertebrate Pests: Feral Pigs (Ed. M. Bomford) Bureau of Resource Sciences, Australian Government Publishing Service, Canberra 163 pp. Infestation of other omnivorous species such as raccoons, collared peccaries, opossums, possums and rodents can give rise to similar adverse agricultural, environmental, financial and health concerns in various countries.

There is therefore a considerable effort focussed on a reduction of the risks posed by feral omnivorous species in Australia, United States, New Zealand and other parts of the world which have unchecked populations of such species.

Despite their impact, the control of omnivores such as feral pigs, possums, raccoons, and rodents is generally time-consuming, ad-hoc and reactive rather than pro-active management. Many techniques are currently employed for mainly localized control (eg shooting, trapping, fencing, etc) however it has been recognized that broad-scale and integrated baiting campaigns are most cost-effective for reducing and maintaining feral omnivore populations at low levels across large areas. Typical baiting campaigns include ground baiting and aerial baiting where the bait is dropped from an aircraft into the loci of the target omnivore population to be controlled.

Lethal baiting campaigns include the use of various poisons, for instance, sodium fluoroacetate (1080) which is placed in or deposited on cereal grains, fermented grain, compressed bran/pollard pellet baits, fresh or dried meat, offal, carcasses, lupin seeds, and fruit and vegetables, and also cyanide in manufactured baits. Of these, the use of soaked or dry wheat grain or fresh meat baits are the most common.

Of the various control means discussed above poison baiting of feral pig and other omnivore populations is recognised as one of the most effective means of controlling such populations and reducing the damage they cause. Unfortunately however, one of the main problems with many of the bait types made from grains or meat and carcass offal or pellets is that they exhibit poor target specificity. Accordingly, while the commonly employed baiting campaigns may prove effective in controlling feral omnivore (eg pig) numbers in a particular area, such campaigns may also adversely affect individuals of other species of animals which may be desired or native species of animals or birds which come into contact with the baits.

Other disadvantages of the present baiting regime can be attributed directly to the specific poison used. For instance, a disadvantage of 1080 is that feral pigs appear to be relatively resistant to the effects of the poison compared to rabbits, foxes, and wild dogs for which it is a more ideal poison. For example, during captive trials with bait delivered 1080, (McIlroy et al, Australian Wildlife Research 16: 195-202) dingos required 0.11 mg/kg to receive an $LD_{50}$ dose whereas feral pigs were reported to require at least 1 mg/kg and some as high as up to 4.11 mg/kg (O'Brien et al, Australian Wildlife Research 15: 285-291).

Moreover, while the terminal toxic events associated with 1080 toxicosis are not thought to be accompanied by conscious pain, there are disturbances in the central nervous system and thus effects on behaviour that can appear unpleasant to the untrained observer. Humans that have recovered from nearly lethal exposures to 1080 have not recalled pain after the event however the final phases of toxicosis have been likened to hypoglycaemic or epileptic fitting. Sodium fluoracetate is presently one of the best toxin choices for feral pig management. However the high doses required for feral pigs mean that this is not a perfectly suitable toxin for pig management.

People poisoned with other poisons such as phosphorus (CSSP) or strychnine have reported substantial pain and suffering and it is highly likely that such poisons are too inhumane to be used to control feral animals such as the pig. Similarly, while warfarin is used therapeutically in low doses for humans suffering from blood clotting disorders and this use is not associated with pain, the use of this anticoagulant in large animals such as feral pigs may give rise to painful haemorrhaging in some animals and therefore it is also not a preferred poison for this application.

This would indicate that none of these poisons and conventionally used food based baits, are perfectly suitable or represent perfectly humane alternatives for eradicating or controlling pest species.

The present invention serves to address at least some of these shortcomings.

SUMMARY OF THE INVENTION

The present invention provides a bait for omnivorous feral animals comprising a solid or semi-solid carrier material and a nitrite salt.

The invention also provides a method for humanely controlling omnivorous feral animals including the step of dispersing within the area of foraging of said omnivorous feral animals at least one bait comprising a solid or semi-solid carrier material and a nitrite salt.

The present invention further provides a method of preparing a bait for omnivorous feral animals comprising a solid or semi-solid carrier material and a nitrite salt, said method comprising:
 (a) mixing carrier material components with a nitrite salt to form a paste or suspended mixture;
 (b) extruding the mixture into a casing; and
 (c) allowing the mixture to at least partially solidify in the casing thereby forming the bait.

DETAILED DESCRIPTION OF THE INVENTION

Figure 1:
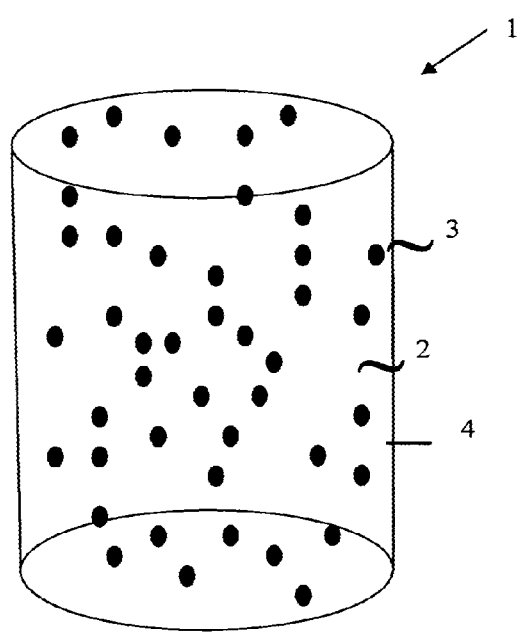
FIG. 1. A diagrammatic illustration of a bait of the present invention.

The term "bait" as used herein refers to the combination of a purposively selected carrier material and active agent for the express purpose of preparing a pest control agent wherein the carrier material and the bait as a whole are palatable and at least partially edible by a target pest. Accordingly, the "bait" of the present invention is a purposely manufactured pest control agent which is to be contrasted with, for instance, a naturally occurring material (eg plant material) which may naturally contain quantities of the active agent.

The invention relates to the humane control of omnivorous feral animals, in particular, feral pigs. Accordingly, the terms "humane" and "humanely" as used herein refer to methods which do not cause undue distress to the target animal species. Signs of distress which are avoided or minimised by the present invention include haemorrhaging, excessive vomiting, vocalisation, severe central nervous system disruption (including hyperexcitability, convulsions, ataxia, leg trembling and leg paddling whilst prone) and prolonged death. Preferably death occurs within 2-3 hours after ingestion of a bait of the present invention.

In relation to the present invention the target pests are omnivorous feral animals, preferably omnivorous feral mammals. More preferably the invention is directed to the control of feral pig and possum populations.

It will be appreciated that the term "feral" as used herein refers to the target pest species (ie omnivorous animals) which live wild such that their population or numbers cannot be easily controlled. In Australia, for instance, many feral animals such as dogs, goats, cats, and pigs, were originally introduced during British settlement as either domesticated species, species suitable for hunting, or where introduced for the purpose of possibly controlling yet other pests. After escaping into the wild such animals have become feral, adopting and flourishing to life unaided by human intervention. Many feral animals are introduced species and their presence in the wild is unwanted as they can adversely affect agricultural endeavours such as crop production and grazing. Feral animals which are introduced species are distinguished from native or domesticated species. These feral animals also invariably cause adverse environmental impact, especially as their populations increase. As such these feral animals have been classified as pests and it is desired to keep populations of such animals to a minimum or, where possible, to completely eradicate them from the wild or from areas of high agricultural or conservation valve. It will be understood that while the bait of the present invention will not be able to distinguish between feral and non-feral domesticated animals, the bait is only intend to be used in the control of feral animal populations and accordingly suitable measures should be taken to ensure that the bait is not distributed amongst domesticated populations.

It will also be appreciated that "feral" also includes overabundant native species who's localised population may require control to mitigate the risk of disease spreading or over browsing of native and/or agriculturally important flora.

The term "active agent" referred to above is an agent which effects the physiology of the target feral animal in a desired manner. The active agent of the present invention is a nitrite salt. Nitrile salts include sodium nitrite, potassium nitrite, as well as amyl nitrite. Most preferably the active agent is sodium nitrite or potassium nitrite and more preferably sodium nitrite. Nitrite salts to be used in the bait of the present invention are commercially available.

It will be appreciated that during typical baiting campaigns multiple baits are dispersed within the area of foraging of the target animal species. A single bait may not provide a lethal dose to a single target animal even if completely consumed. Preferably however the nitrite salt is in an amount which provides a lethal dose to a target feral animal. That is, the quantity of nitrite salt in a single bait is such that it will effectively kill a feral omnivorous animal.

It would be appreciated that the lethal dose of a nitrite salt to kill a feral omnivorous animal will typically depend on the species physiology and weight. In respect of feral pigs the lethal dose is preferably at least 135 mg/kg of nitrite salt. Accordingly, for a feral pig weighing 60 kg, to provide a lethal dose a single bait would need to comprise at least 8.1 g of the nitrile salt. More preferably the lethal dose is between 270-540 mg/kg. Accordingly, as most adult feral pigs encountered under typical conditions may weigh anywhere between approximately 30-300 kg the preferred amount of nitrite salt in a single bait is between 8.1 g-162 g. More preferably the preferred amount of nitrite salt in a single bait is less than 30 g and even more preferably less than 20 g, for instance less than 15 g.

For feral possums the lethal dose is preferably also at least 135 mg/kg and more preferably at least 163 mg/kg. More preferably the lethal dose is between 400-600 mg/kg. The preferred amount of nitrite salt in a single bait is between 1.9 g-4.9 g.

The nitrite salt may comprise up to 25% by weight of the total weight of the bait. Preferably the nitrite salt comprise up to 15% by weight of the total weight of the bait.

The bait of the present invention is also composed of a solid or semi-solid carrier material. The carrier material is designed to be attractive, palatable and edible to the target feral animal and as such will generally contain or consist of a component, or mixture of components, which is a potential food source for the target feral animal. In addition the bait should be of a consistency suitable for consumption by the target animal but sufficiently robust as to enable easy storage and transport and also preferably able to survive intact the forces that arise on hitting the ground during aerial deployment from fixed wing or helicopter aircraft.

For the present invention which is directed to the control of feral omnivores, such as feral pigs, the carrier material is selected from food sources which are attractive, palatable and edible to the target omnivore. For example, the carrier material may contain or consist of animal or plant derived components and any combination of these.

Examples of suitable animal components include fish meal, bone, meat, offal, skin, egg, milk proteins, casein, and fat.

Examples of suitable plant derived components include pollard, bran, maize (corn), plant fibres, flour, fruit, vegetables, seeds, cereal and straw.

Preferably the carrier material is selected with non-target species in mind such that the potential uptake of the bait by non-target species is reduced. Thus, the selection of the particular type and amount of components which make up the carrier material may vary depending on the non-target species which are to be avoided. For instance, in the case where the non-target species are herbivores (e.g. specific bird species, marsupials, etc) the carrier material may be selected to comprise of mainly animal derived components. This is particularly preferred when targeting feral pigs in Australia where the majority of non-target native species have a restricted dietary range and where many non-target species are obligate herbivores or graniferous birds that are less attracted to am omnivore bait.

The carrier material may also include specific chemical attractants, such as flavourants or scented substances (odourants). The chemical attractant may be a natural or artificial essence, such as banana, honey, aniseed, molasses, cinnamon oil and chocolate. The carrier material may also comprise other additives known in the art such as colourants, preservatives, binders, fillers, pH adjusters and the like. For instance, in a preferred embodiment the carrier material contains a colourant (dye) which makes the bait green in colour to mask the bait from non-target species such as birds which generally have a preference for eating yellow and red coloured food consistent with ripe fruit. Also, preservatives and binding agents may be added to provide mechanical strength to the finished bait and to reduce the risk of premature degradation on storage.

Furthermore, in order to increase the target specificity the bait may also include repellants of other non-target species such as methyl anthranilate which is a known bird repellant.

Without wanting to be bound by theory it is believed that the nitrite salt in the bait acts by causing methaemoglobin (Met Hb) formation in red blood cells, which prevents oxygen transport, and at specific doses causes rapid death by methaemoglobinaema. Accidental death by nitrite poisoning has been reported for domestic livestock such as pigs (see, for instance, Vyt, P et al., Viaams Diergeneeskundig Tijdschrift, 2005, 74, 359-363; Gibson. R., The Veterinary Record, Mar. 22, 1975, p 270; McParland, P. J., et al., The Veterinary Record, Mar. 1, 1980, p 201; Counters, D. E., et al, The Veterinary Record, May 3, 1975, p 412; Winks, W. R., The Queensland Journal of Agricultural Science, Vol. 7, No. 1 and 2, March and June 1950, pp 1-14; and London, W. T., et al, J.A.V.M.A, Vol 150, No. 4, pp 398-402.

From a report on the study of methemoglobin formation and reduction in various animals (see Smith & Butler., Am. J. Physiology. 210(2):347-350, 1966) it appears that the susceptibility to Met Hb formation may be related to the Met Hb reduction rate in such a way that a rapid Met Hb formation rate is offset by a rapid Met Hb reduction rate. In this study it was observed that pigs were particularly susceptible to methaemoglobinaemia because of the pigs inability to effectively reduce Met Hb. The reason for this is that pigs possess uniquely low levels of methaemoglobin reductase which makes them highly susceptible to methaemoglobin forming compounds.

Accordingly, the manufactured baits of the present invention are particularly suitable for the control of omnivorous feral animals (like for instance feral pigs and possums) that are sensitive to methaemoglobinaemia due to physiologically low levels of methaemoglobin reductase or low activity of this enzyme.

The susceptibility of some omnivorous species to sodium nitrite (SN) has been compiled by the present inventors and is outlined in Table 1 below:

TABLE 1

| Species | NADH-Methb Reductase levels | Approximate gavage lethal dose (mg/kg) | Approximate bait lethal dose (mg/kg) | Body size (kg) | Approximate lethal SN dose (gm) |
|---|---|---|---|---|---|
| Marsupials | | | | | |
| Common brushtail possum | 30.6 | 163 | 489 | 4 | 2.0 |
| Northern brown bandicoot | 52 | 232 | 696 | 2 | 1.4 |
| Eutherians | | | | | |
| Pig | 12 | 103 | 310 | 50 | 15.5 |
| Rat | 10 | 97 | 291 | 0.1 | 0.03 |
| Raccoon | — | — | 150 | 3 | 0.75 |
| Mouse | 53 | 235 | 705 | 0.03 | 0.02 |

It has now also been identified that not only do nitrite salts act as effective toxins, poisoning and death occur rapidly and relatively painlessly. The mechanism of action provides the quick development of anoxia in the brain due to the reduced oxygen carrying capacity of methaemoglobin induced by the nitrite. Thus one of the first symptoms of the toxicosis is the occurrence of unconsciousness, in much the same way as carbon monoxide acts. Carbon monoxide has been used as a method to humanely dispose of unwanted animals and is considered to be one of the most humane techniques available for this process. This is to be contrasted with the severe clinical symptoms experienced with warfarin (bleeding in various organs leads to pain, eg lameness, etc), phosphorous (eg liver failure leading to slow lingering death which results in feeling sick for a long period of time, etc) and 1080 (unconsciousness, seizures and recovery in between seizures which often can lead to injury in between seizures) poisoning. Also the speed of death is very quick with nitrite so any symptoms are only experienced for a short period of time. Accordingly, an advantage of the baits of the present invention are that they provide a more humane alternative to existing feral omnivore baits.

Accordingly, in another aspect the present invention relates to a bait for humanely controlling feral omnivores comprising a solid or semi-solid carrier material and a nitrite salt wherein the nitrite salt is in an amount which provides a lethal dose to a feral omnivore.

In order to enhance or supplement the methaemoglobin forming capabilities of the nitrite salt and hence the lethality of the baits of the present invention, the bait may also include additional methaemoglobin forming substances. Such substances include direct oxidants of haemoglobin such as other nitrites like amyl nitrite, or methylene blue, toluidine blue and sodium thiosulphate. Indirect oxidants may also be included such as aminophenols (for instance, o-aminophenyl, p-aminophenol, m-aminophenol), alanine, metaxylidine, hydroxylamines (for instance, phenylhydroxylamine), hydrazines, acetanilide, acetophenetidin, m-phenylenediamine, nitrosobenzene, nitrobenzenes (for instance, o-dinitrobenzene, p-dinitrobenzene, m-dinitrobenzene, trinitrobenzene, o-nitrotoluol, m-nitrotoluol, p-nitrotoluol, 2,4-dinitrotoluol, 2,6-dinitrotoluol, 2,4,6-trinitrotoluol, m-chloronitrobenzene, m-aminonitrobenzene, 2,4-dinitrochlorobenzene, and p-nitro-o-toluidine), sulphonamides (for instance, sulphanilamide), quinones, p-aminoacetophenone, napthalene, dimethylaminopyridine (4-DMAP), aminopropiophenones (for instance, p-aminopropiophenone). These substances may individually or collectively enhance or potentiate the development of methaemoglobin or may slow the conversion (reduction) of induced methaemoglobin back into normal haemoglobin.

The active agent may be used in combination with the carrier material in any manner which will allow for the delivery of the active agent to the target pest. For instance, the active agent may be incorporate substantially within the carrier material or coated on the surface of the carrier material.

In one embodiment the carrier material may be grain seeds which have been soaked or coated with the nitrite salt or intimately mixed with the nitrite salt.

In a further embodiment the bait of the present invention may take the form of a piece of meat (eg part of a carcass) in which the nitrite salt is coated to the surface of the meat or is incorporated within the meat, for instance, by injecting a solution or dispersion of the nitrite salt into the meat.

In a preferred embodiment the nitrite salt is simply dispersed throughout the carrier material to form the bait. More preferably the nitrite salt is evenly dispersed throughout the carrier material. Dispersion may be accomplished by simple mixing of the carrier material with the required amount of nitrite salt.

Bait 1 as shown in FIG. 1 is cylindrical in shape and includes a solid carrier material 2 which has sodium nitrite 3 evenly dispersed throughout. The solid carrier material, and hence the bait, is strengthen by a thin casing 4 which covers the outer circumference of 1.

In another embodiment the solid or semi-solid carrier material forms the outer surface of the bait and may be in physical contact with a core which contains the nitrite salt. Thus in this embodiment the core containing the active agent is located within the solid carrier material and not dispersed throughout. This may include a plurality of cores. It will be appreciated that the core containing the active ingredient is housed internally of the carrier material such that preferably no surface of the core protrudes from the carrier material. Preferably the core is located centrally within the solid carrier material. More preferably the core is located centrally within the solid carrier material such that no surface of the core is exposed to the outside environment. Therefore, the solid carrier material completely covers or surrounds the core which is located therein.

Figure 2:
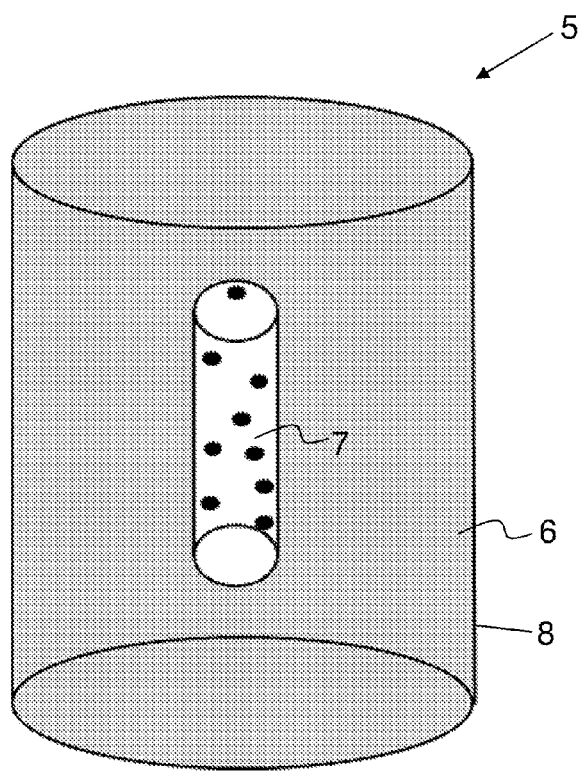
FIG. 2. A diagrammatic illustration of a bait of the present invention.

Bait 5 as shown in FIG. 2 is cylindrical in shape and includes a solid carrier material 6 in physical contact with and a centralised core 1 which is completely covered or surrounded by the carrier material such that no surface of the core is exposed to the outside environment. The solid carrier material, and hence the bait, is strengthened by a thin casing 8 which covers the outer circumference of 5.

The main advantage of having the core located within the solid or semi-solid carrier material is that smaller non-target animals or animals that merely sample the bait carrier material cannot readily access the core and hence the active agent. This makes the bait more target-specific.

It would also be appreciated that the phrase "the core contains an active agent" means that the core does not, to any great extent, allow the release of the active agent (nitrite salt) into the surrounding carrier material. This feature will assist in preventing consumption by non-target animals. Accordingly, the active agent is present in the core as an encapsulated or bound active agent. Thus the core may be composed of any suitable material which is able to contain the active agent. However it is desirable that the core material is of a consistency and flavour that is readily consumed by the target animal. For instance the core may include encapsulating matrix forming materials which are used in, for instance, the pharmaceutical industry. Typical encapsulating materials include, gelatin, carbohydrates (including polysaccharides and monosaccharides), fatty acids, waxes and tallow.

As discussed above in one embodiment the bait of the present invention comprises a core which is preferably "in physical contact with a solid or semi-solid carrier material". This means that there is no physical barrier separating the core from the carrier material. This becomes only possible because the core is made of suitable ingredients which do not allow the active agent (to any great extent) to permeate into the surrounding carrier material. Thus another benefit of the present invention is that the core does not need to be coated with a coating material (eg, shellac material or acrylate polymer) in order to contain the active agent within the core. This allows for ease in manufacturing which in turn provides certain manufacturing cost benefits. This also increase the likelihood of consumption by the target animals, for example feral pigs, since pigs mouth the bait material before eating and can reject hard or unnatural components within a bait.

In this embodiment the core may be made up of hydrophobic ingredients such that there is limited exchange of water between the core and carrier material. It is also desirable for the core to be stable upon storage but that it becomes vulnerable to weathering and biological degradation in the field so that the baits do not persist in the environment for extended periods. It is also desirable that the core is sufficiently thermally stable so that the core ingredients do not melt or leach into the carrier material when the baits are deployed in hot areas where there is direct exposure of the bait to summer sunshine. The core is composed of ingredients such that the active agent (nitrite salt) is contained therein and so the core maintains limited stability when the bait is exposed to normal environmental conditions.

As the core is also intend to be attractive, palatable and edible to the target animal, the core may also comprise attractants, such as flavourants or odourants. In addition the core may also comprise other additives known in the art such as preservatives, binders, humectants, fillers, pH adjusters and the like. For instance, in order to preserve the activity of the active agent upon storage, transport and use, antioxidants may be added to the core during manufacture of the bait. Typical antioxidants include sodium benzoate, sodium metabisulphite and the like.

The preferred baits of the present invention may be formed by conventional techniques used for forming pellets or tablets in the pharmaceutical or agrochemical industry. It would be evident to the skilled person that the actual shape of the bait is not a crucial parameter and that any obtainable shape is within the scope of the present invention. However, a particular shape may be advantageous, when for instance, the bait is being used in an aerial baiting campaign. For example, a specific shape may act to enhance the aerodynamics or physical strength of the bait and allow for more precise dispersement.

Also, the size and shape of the bait may further enhance target specificity. For instance, larger baits for larger animals would decrease the likelihood that smaller non-target species could carry the bait or that enough of the bait could be consumed to provide a lethal dose.

The preferred baits of the present invention may be formed, for instance, by direct compression or by simple extrusion processes using an Archimedes screw extruder.

In the latter system the extrusion is accomplished by an Archimedes screw that compresses the carrier mixture through a shape forming nozzle or into an outer casing. The extruder carrier may be cut or divided as it is extruded or may be allowed to partially or fully solidify before the carrier is cut to desired lengths to provide baits of different sizes or weights. The cutting may be achieved by slicing means (eg fixed knives) to control the length of the resulting baits. The diameter and longitudinal shape of the bait pellets can be controlled by the diameter and shape of the nozzle apertures and the outer skin used to contain the bait.

To aid in the manufacturing process according to the above procedure further additives or excipients may be added such as water or binders such as starch, gelatin or gum arabica. Lubricants may also aid in the aforementioned pellet production.

In a further embodiment the carrier material is formed by initially weighing and blending all dry ingredients in a mixer/extruder. The liquid ingredients are then added and mixed in order to form an extrudable paste or suspension. The nitrite salt may be added to the paste and suspension and mixing continued to disperse the salt.

The mixture is then extruded into a thin casing in order to provide the carrier material with a particular form once the carrier material sets solid. Preferred casings include non and semi-permeable natural and synthetic polymer films which are edible such as synthetic cellulose film casings. The use of a casing in this manner is especially preferred where the bait is to be used in aerial baiting campaigns as the casing provides the bait with added strength (impact resistance) when it is dispersed from the air. The casing is also preferred because it improves the ease of handling and also aids in reducing non-target uptake and may also be manufactured with printed labels to provide additional labelling and safety information as appropriate or to further camouflage the bait to reduce uptake by non-target species. Casings which are biodegradable (such as synthetic cellulose film or natural collagen casings) are advantageous because they allow baits which have not been consumed, or partially consumed, to degrade naturally, although it is recognised that other materials such as plastic skins could be used. This also reduces the likelihood of the bait being consumed by non-target species. In this embodiment it is typically also preferred that the casing is coated with an attractant so that the bait retains its attractiveness to the target animal. For instance, the casing may be coated with fish oil or other attractants.

The preferred baits of the present invention where the nitrite salt is evenly dispersed throughout the carrier material may be made by the above process. For the embodiment where the nitrite salt is contained in a core, the manufacture of the shaped solid carrier material is completed, without the addition of nitrite salt and the core. This may be done by punching a hole within the shaped solid or semi-solid carrier material to form a dosing well ready for core insertion. The ingredients of the core (including the nitrite salt) may be introduced into the well as a liquid, suspension, or paste which solidifies partially or completely after insertion. Alternatively, the core may be shaped and allowed to solidify (either partially or completely) and then inserted into the dosing well. Accordingly, in an embodiment the core may be prepared by introducing the core ingredients into a casing material to form a core shape amendable to insertion into the dosing well. In this embodiment the core casing would also need to be prepared from a material which is edible. Accordingly such an embodiment would mean that the core and carrier material are physically separated by casing material.

Preferably, a plug of the same carrier material is then inserted into the dosing well or the well otherwise closed over after dosing the carrier material with the core components so that the core is not exposed to the external environment.

Accordingly, another aspect of the invention provides a bait for omnivorous feral animals with an outer edible layer comprising a core and a solid or semi-solid carrier material wherein the core contains a nitrite salt as an active agent and the core is located within the solid or semi-solid carrier material.

The present invention further provides a method of preparing a bait for omnivorous feral animals comprising a core in physical contact with a solid or semi-solid carrier material wherein the core contains a nitrite salt as an active agent and the core is located within the solid or semi-solid carrier material, said method comprising:

(a) mixing carrier material components to form a paste or suspended mixture;
(b) extruding the mixture into a casing;
(c) allowing the mixture to at least partially solidify in the casing thereby forming the solid or semi-solid carrier material;
(d) forming a dosing well within the solid or semi-solid carrier material;
(e) mixing core ingredients and active agent to form a liquid or suspension or preparing a solid form core;
(f) partially filling the dosing well with the liquid, suspension or solid form core of step (e); and
(g) plugging the remaining volume of the dosing well with the solid or semi-solid carrier material.

The invention also provides a method for humanely controlling omnivorous feral animals including the step of dispersing within the area of foraging of said omnivorous feral animals at least one bait according to the present invention.

The baits of the present invention are particularly suited for target specific ground or aerial baiting regimes. The method preferably employed includes identifying a target feral animal population and distributing a quantity of the bait within the loci or area where the feral animals forage.

The quantity of bait distributed will depend on the number of target animals in the population to be controlled.

As mentioned previously one of the advantages of the bait of the present invention is that it may be presented in a form which is more target specific than existing baits. In order to further increase target specificity, one can design a baiting campaign which is better aimed at the desired feral animal.

For instance, feral pigs are required to access water on a daily basis. Accordingly, baits may be dispersed around known watering points in drier areas or at drier times of the year. Also, feral pigs have a nocturnal or crepuscular lifestyle, therefore dispersing baits in the late afternoon may aid in minimising contact with non-target species. Furthermore, feral pigs are also known to have very large, nearly completely overlapping home ranges. Thus, placing groups of bait well apart may also aid in minimising non-target fatalities.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Certain embodiments of the invention will now be described with reference to the following examples which are intended for the purpose of illustration only and are not intended to limit the scope of the generality hereinbefore described.

EXAMPLES

Example 1

Preparation of a Bait with a Hydrophobic Toxic Core a) Formulation Components

Sodium Nitrite sufficient to give 25 grains per bait, Wax, Tallow, Propylene glycol, Water, Salt, Sugar, Gelatine, Citric acid, Potassium sorbate, Sodium benzoate, Sodium metabisulphite, Brilliant blue dye, Fish meal, Maize, Flour, Pollard, Tuna oil, and Fibrous casings (tuna oil coated).

b) Formulation Process

Stage 1 Mixing

The dry ingredients for the carrier material may be first weighed then blended dry for one minute in a two directional ribbon mixer/extruder. The tuna oil and tallow may be added followed by the pre-heated (80° C.) liquid ingredients (containing all water-soluble additives except the poison) and mixing continued for 3 minutes until a uniform consistency and colour is achieved.

Stage 2 Extrusion and Cooling

The warm mixture may be extruded into 55 mm diameter synthetic cellulose casings, which may be coated with a small quantity of tuna oil, into lengths and allowed to cool and solidify to a firm rubbery consistency overnight.

Stage 3 Cutting

The solidified long casing extrusions may be cut to the required lengths to form shaped carrier material of approximately 240 grams weight that are approximately 90 mm long and 55 mm diameter.

Stage 4 Formation of Dosing Well in Shaped Carrier Material for Core Insertion

The cut and shaped carrier material may be transferred to a hole punching ram that forms a slightly tapered cylindrical dosing well of approximately 15 mm diameter through the centre of the carrier material from one cut end, to within 2 cm of the bottom of the shaped carrier material.

Stage 5 Preparation of the Core Containing Sodium Nitrite

A freshly prepared suspension of sodium nitrite in a hydrophobic mixture of wax and prime tallow may be formulated at 80° C. in a melted state and transferred to a precision metering pump fitted with a thermostatically controlled jacketed tank where the mixture is constantly agitated while maintained at 70-80° C.

Stage 6 Dosing and Closing

The sodium nitrite suspension may then be pumped via a vernier calibrated metering pump to the bottom of the dosing well, where it can be allowed to solidify. A 10 mL volume of the suspension may deliver a nominal dose of 25 grams of sodium nitrite per bait. The open end of the dosing well may then be closed over with carrier material by a second ram to secure the poison core within the carrier material and away from the bait ends.

Stage 7 Packing and Batch Numbering

The finished baits may then be packed into high strength 20 liter polypropylene tubs fitted with rubber sealed tamper evident lids and labelled with approved labels and date of manufacture, batch number and expiry date.

Example 2

Preparation of a Bait with a Sodium Nitrite/Honey Toxic Core a) Formulation Components Sodium Nitrite sufficient to give 25 grams per bait, Propylene glycol, Water, Salt, Sugar, Gelatine, Honey, Citric acid, Potassium sorbate, Sodium benzoate, Sodium metabisulphite, Brilliant blue dye, Fish meal, Maize, Flour, Pollard, Tuna oil, and Fibrous casings (tuna oil coated).

b) Formulation Process

Stage 1 Mixing

The dry ingredients for the carrier material may be first weighed then blended dry for one minute in a two directional ribbon mixer/extruder. The tuna oil and tallow may be added followed by the pre-heated (80° C.) liquid ingredients (containing all water-soluble additives except the poison and honey) and mixing continued for 3 minutes until a uniform consistency and colour is achieved.

Stage 2 Extrusion and Cooling

The warm mixture may be extruded into 55 mm diameter synthetic cellulose casings, which may be coated with a small quantity of tuna oil, into lengths and allowed to cool and solidify to a firm rubbery consistency overnight.

Stage 3 Cutting

The solidified long casing extrusions may be cut to the required lengths to form shaped carrier material of approximately 240 grams weight that are approximately 90 mm long and 55 mm diameter.

Stage 4 Formation of Dosing Well in Shaped Carrier Material for Core Insertion

The cut and shaped carrier material may be transferred to a hole punching ram that forms a slightly tapered cylindrical dosing well of approximately 15 mm diameter through the centre of the carrier material from one cut end, to within 2 cm of the bottom of the shaped carrier material.

Stage 5 Preparation and Dosing of the Core Containing Sodium Nitrite

A freshly prepared mixture of sodium nitrite and honey may be added to the dosing well.

Example 3

Preparation of a Bait with Toxin Dispersed Through Carrier a) Formulation Components Sodium Nitrite sufficient to give 25 grams per bait, Propylene glycol, Water, Salt, Sugar, Gelatine, Citric acid, Potassium sorbate, Sodium benzoate, Sodium metabisulphite, Brilliant blue dye, Fish meal, Maize, Flour, Pollard, Tuna oil, and Fibrous casings (tuna oil coated).

b) Formulation Process

Stage 1 Mixing

The dry ingredients for the carrier material including the sodium nitrite may be first weighed then blended dry for one minute in a two directional ribbon mixer/extruder. The tuna oil may be added followed by the pre-heated (80° C.) liquid ingredients and mixing continued for 3 minutes until a uniform consistency and colour is achieved.

Stage 2 Extrusion and Cooling

The warm mixture may be extruded into 55 mm diameter synthetic cellulose casings, which may be coated with a small quantity of tuna oil, into lengths and allowed to cool and solidify to a firm rubbery consistency overnight.

Stage 3 Cutting

The solidified long casing extrusions may be cut to the required lengths to form shaped carrier material of approximately 240 grams weight that are approximately 90 mm long and 55 mm diameter.

Stage 4 Packing and Batch Numbering

The finished baits may then be packed into high strength 20 liter polypropylene tubs fitted with rubber sealed tamper evident lids and labelled with approved labels and date of manufacture, batch number and expiry date.

Example 4

Trial Data

Pen Trials

The captive feral pig colony at Robert Wicks Pest Animal Research Centre (Queensland Department of Natural Resource, Mines and Water) was comprised of feral pigs harvested by commercial harvesters in the area surrounding Inglewood, Queensland. A variety of sexes, ages and sizes were drawn at random from the captive colony and used in these trials. Feral pigs were housed in the purpose built feral pig accommodation. Two distinct trials occurred to test sodium nitrite as a poison for feral pigs. One trial delivered sodium nitrite to anaesthetised feral pigs by gavage (proof of concept trial), and a second trial delivered sodium nitrite to feral pigs in food (bait delivery trial).

Proof of Concept Trial

Figure 5:
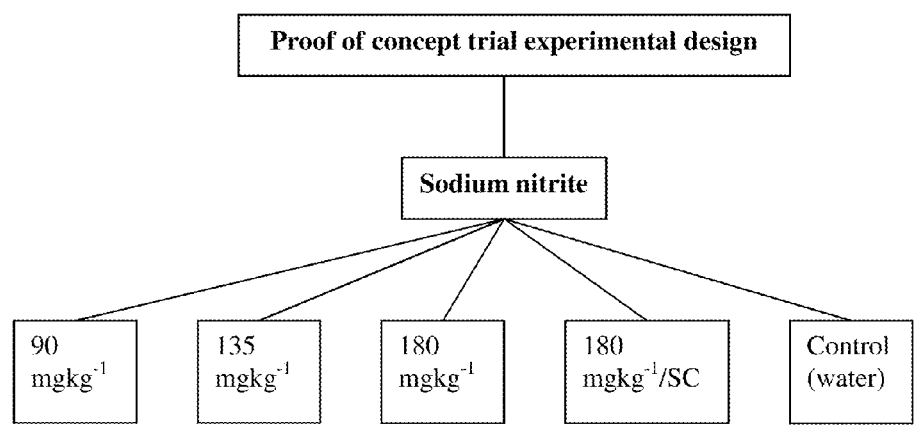
FIG. 5. Flow chart demonstrating experimental design of proof of concept of trial.

This trial occurred in January 2006. The trial design is set out in FIG. 5. Twenty-one fasted captive feral pigs were anaesthetised with ketamine (20 mgkg$^{-1}$) and xylazine (1.2 mgkg$^{-1}$) by intramuscular injection with a 16 gauge needle into the quadriceps muscle. A known quantity of sodium nitrite was prepared for each pre-weighed feral pig and dissolved or suspended in isotonic water (15-70 mls). The resulting liquid was then administered by oesophageal gavage to an individual feral pig. A number of sodium nitrate dosages were trialled on different groups of feral pigs. After administration, feral pigs were observed carefully for clinical signs and death. The dosing regime for sodium nitrite is outlined in FIG. 5 (each dose rate contained three feral pigs).

Three untreated feral pigs functioned as placebos. They were anaesthetised, gavaged with 15 ml of isotonic water, and underwent veni-puncture from the internal or external jugular vein. Specifically, an 18 gauge, 1 inch needle was inserted into the caudal part of the jugular groove near the manubrium and suction was provided by a 3 ml syringe. The feral pigs were then allowed to recover from the anaesthetic in the same situation as other feral pigs in the trial, but without further veni-puncture. Control and recovered feral pigs were euthanased by a rifle shot. A post mortem examination was conducted on these feral pigs and appropriate specimens collected.

Sodium nitrite (NaNO$_2$), referred to as SN hereafter, was administered to twelve anaesthetised feral pigs with or without sodium carbonate, by gavage with a stomach tube. This was done on an identical manner to the placebo feral pigs. Specifically, three feral pigs received 30 g of sodium carbonate (administered with 25 ml of isotonic water) followed immediately by 180 mgkg$^{-1}$ of SN, dissolved in 15 ml of water. Three feral pigs received only 18 mgkg$^{-1}$ of SN in 15 ml of water. Three feral pigs were administered SN at 135 mgkg$^{-1}$ in 15 ml of water. A final three feral pigs were administered 90 mgkg$^{-1}$ of SN in 15 ml of water.

SN dosed feral pigs (not the 135 mgkg$^{-1}$ group) were blood sampled within 1 min of administration of the toxin. Feral pigs were then sampled opportunistically at various times over the following minutes or hours. Smaller feral pigs were blood sampled more frequently, but were sedated or were semi-conscious due to effects of SN when blood sampling occurred. Feral pigs which recovered from anaesthetic quickly, or were large, were sampled less frequently than other feral pigs. All feral pigs were also blood sampled immediately after death (within 1 minute). The blood samples were used to assess Methaemoglobin levels (Met 315 Hb). An automated radio-oximeter (model ABL520 supplied by Radiometer Copenhagen) was used for blood Met Hb analysis. The Met Hb data from each individual within a group was pooled to provide dose response curves for multiple feral pigs administered at a single dose rate. The feral pigs which received 135 mgkg$^{-1}$ were not blood sampled until after death. A post mortem examination was conducted on all feral pigs.

For SN poisoned feral pigs mean times to death and peak Met Hb levels were calculated. A Kruskal-Wallis statistical test was used to determine any significant differences between the time to death at different doses of SN, with or without sodium carbonate. Serial Met Hb levels were pooled for each group of feral pigs receiving a single dose rate and plotted against time. Trend-lines were fitted to the data. Logarithmic functions were used for the three higher dose rates, while a polynomial trend line was fitted to the 90 mgkg$^{-1}$ feral pig group. This provided a visual representation of the effect of different doses of SN and the possible synergist (sodium carbonate) on Met Hb levels. Multidimensional scaling and ANOSIM tests were conducted on data generated from SN killed feral pigs using Primer (V.5) (Clarke and Gorley 2001 PRIMER V.5: User manual/tutorial. PRIMER-E: Plymouth UK.; Clarke and Warwick 2001 Change in marine communities: an approach to statistical analysis and interpretation, 2nd edition, PRIMER-E Ltd, Plymouth UK). This program makes few assumptions about data and consists of a range of univariate, multivariate and graphical routines for analysing matrices of samples. Specifically, ordination by multidimensional scaling (MDS) was used to visually differentiate feral pigs based on variables (time to death, peak Met haemoglobin levels, time to dyspnoea and time to vomiting). One factor was used, dose rate. Data was normalized and 30 random resets occurred. ANOSIM was used to determine whether significant differences between these variables were due to dose rate. SIMPER (a function of Primer) was used to determine dissimilarity between dose rates, or what dose rates were most dissimilar.

Bait Delivery Trials

Figure 6:
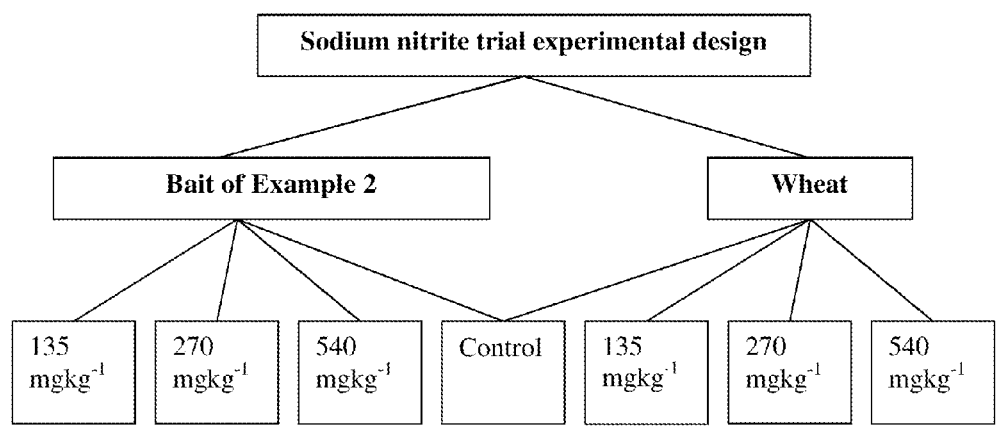
FIG. 6. Flow chart demonstrating experimental design of toxins in feed trial.

The trials were conducted in October 2005 and June 2006. Both trials were designed to test the hypothesis that SN would be lethal to feral pigs when they consumed the toxin freely in food. During the second trial (see FIG. 6-*each* dose rate contained six animals divided evenly among two bait carrier materials; six controls were used) to test sodium nitrite, 24 feral pigs were used. Before the toxin trial, each feral pig was pre-fed daily for 10 days with the bait substrate they were to receive during the toxin trial (bait or dry wheat). During the trial, six feral pigs acted as controls, receiving no toxin, but receiving bait substrate (carrier material). Three of these received wheat and three received the manufactured baits of the type described in Example 2. The remaining 18 feral pigs were divided into three groups of six animals. Three pigs in each group received 250 or 500 g (depending on body size and therefore total toxic dose to deliver) of wheat and the other three received one or two the baits (again, amount of toxin dependent). Each successive group of 6 feral pigs received increasing doses of sodium nitrite at 135 (lowest successful gavage dose), 270 and 540 mgkg$^{-1}$. Feral pigs were observed every 15 minutes for 6 hours, then hourly for 6 hours, then at euthanasia 12 hours after clinical signs developed (if they remained alive).

Results

Pen Trials

Proof of Concept Trial

Placebo Feral Pigs.

The placebo feral pigs all survived anaesthesia, blood sampling and gavage. The clinical signs were exclusively due to the anaesthesia. These included unconsciousness that lasted 30-50 min. All three animals attempted to stand by 60 min, post administration of the anesthetic for sampling and all animals were standing normally by 75-120 min. At three hours after the injection of the anaesthetic agent, all feral pigs were standing, walking, eating and drinking, and appeared normal. These animals were euthanased by rifle shot at 3 hr post anaesthesia. Post mortem findings were unremarkable after a thorough examination of thoracic and abdominal organs, and examination of skeletal muscles and subcutaneous tissues. The only abnormality detected was small haematomas in the quadriceps associated with the injection of the anaesthetic material via jab pole.

Sodium Nitrite Feral Pigs.

Twelve feral pigs were administered SN (and three of these also received sodium carbonate). Initial Met Hb levels were close to zero for all feral pigs at the time of administration of SN. However, administration of SN caused rapid increases in blood Met Hb values in all feral pig that were sampled. The three higher doses appeared to cause more rapid and larger rises in blood Met Hb than the low dose (90 mgkg$^{-1}$, see FIG.

3). The plotted line of best fit for each treatment group appears to suit the data well with no $r^2$ value less than 0.88. Sodium carbonate did not appear to act as a synergist with animals that received this having similar curves to groups which received only high doses of SN.

All nine feral pigs that received doses of 135 mgkg$^{-1}$ or above died. The mean time to death was 106±75 (S.D.) min (range 42-130). The mean peak Met Hb level in killed feral pigs was 82%. Only one of three feral pigs administered SN at 90 mgkg$^{-1}$ died. The single death occurred immediately following blood sampling after Met Hb levels had begun to decline, and is possibly the result of oxidative stress during handling. Feral pigs that were poisoned with higher doses appeared to die more quickly (see table 2). However, times to death between the three lethal treatments (180 mg/kg, 180 mg/kg (with sodium carbonate) and 135 mg/kg) were not significantly different when examined with a Kruskal-Wallis test (K=5.067, d.f.=2, P=0.079).

TABLE 2

Figure 3:
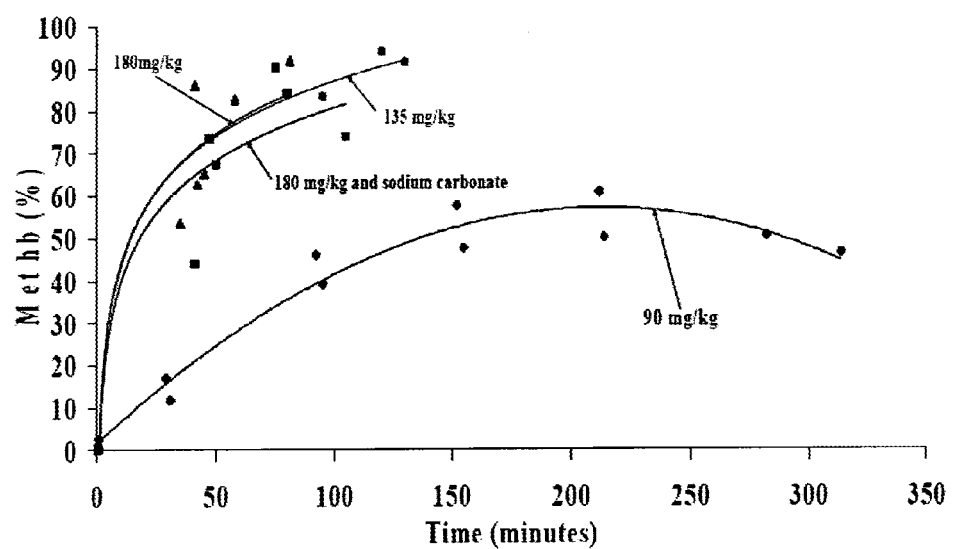
FIG. 3. Trace of blood Met Hb levels of feral pigs poisoned with sodium nitrite. Plot of the % Met Hb level in blood as a function of time (minutes) for feral pigs poisoned with sodium nitrite at levels of 90, 135, 180, and 180 (plus $Na_2CO_3$) respectively.

Dose rates, outcome and peak Met Hb levels[1] for each feral pig group administered SN (see FIG. 3)

| Dose rate (mgkg$^{-1}$) | Sex ratio (M:F) | Weight ± S.D. (kg) | Death/ survival | Mean time to death (minutes) | Mean peak Met hb (%)[1] |
|---|---|---|---|---|---|
| 0 (placebo) | 0:3 | 46 ± 12 | 0/3 | NA | NA |
| 90/NaNO$_2$ | 2:1 | 34 ± 30 | 1/2 | NA[2] | 55[3] |
| 135/NaNO$_2$ | 1:2 | 35 ± 9 | 3/0 | 115 ± 18 | 89 ± 6 |
| 180/NaNO$_2$ | 2:1 | 26 ± 16 | 3/0 | 87 ± 16 | 83 ± 8 |
| 180/NaNO$_2$ (with Na$_2$CO$_3$) | 2:1 | 30 ± 16 | 3/0 | 52 ± 26 | 80 ± 15 |

[1]This is the approximate peak level since sampling time may not have coincided with the time of peak Met Hb. However, after graphing and fitting a 'line of best fit' these values appear to be approximately peak values.
[2]The single individual that died took 302 minutes, although the death was likely precipitated by handling during partial metheamoglobinanemia.
[3]Two from three animals were assessed.

In the proof of concept trial it was sometimes difficult to distinguish which clinical signs were due to anaesthesia and which were due to intoxication. Comparison with placebo feral pigs assisted with this. There were two groups of feral pigs when considering clinical signs in nitrite intoxicated feral pigs. One group exhibiting common signs were the nine feral pigs which received ≥135 mgkg$^{-1}$, and the second group were the three feral pigs that received 90 mgkg$^{-1}$.

The feral pigs which received higher doses generally did not recover fully from anaesthesia and died rapidly, with minimal clinical signs. Two of these nine animals recovered consciousness, and attempted to stand before the full effects of the SN became apparent and they again appeared to lose consciousness. Seven animals vomited between 1-4 times when they were conscious, but retching was not prolonged. Most animals became dyspnoeic approximately 30-60 minutes after gavage, and this gradually worsened until marked gasping occurred just before death. In-coordination, paddling and short convulsive seizures occurred in two of nine animals, and this was apparent close to the time when these feral pigs died. The feral pigs which received lower doses showed a prolonged period of lethargy which lessened gradually over 4-6 hours. Vomiting occurred in two of three animals, three hours after intoxication. One animal died approximately 5 hours after dosing, following blood sampling. Two feral pigs survived after receiving 90 mg/kg doses of SN and had near zero Met Hb levels 14 hours post administration.

Figure 4A:
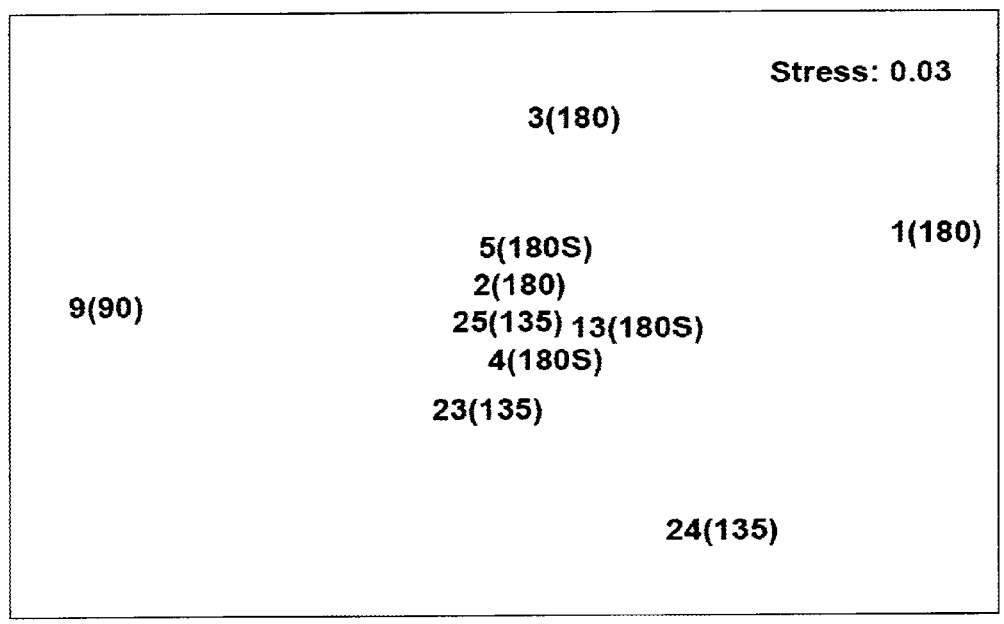
FIG. 4a. Multidimensional scaling analysis trace highlighting the dissimilarity between feral pig dose rate groups base on all pair wise coefficients as calculated with SIMPER analysis.
Figure 4B:
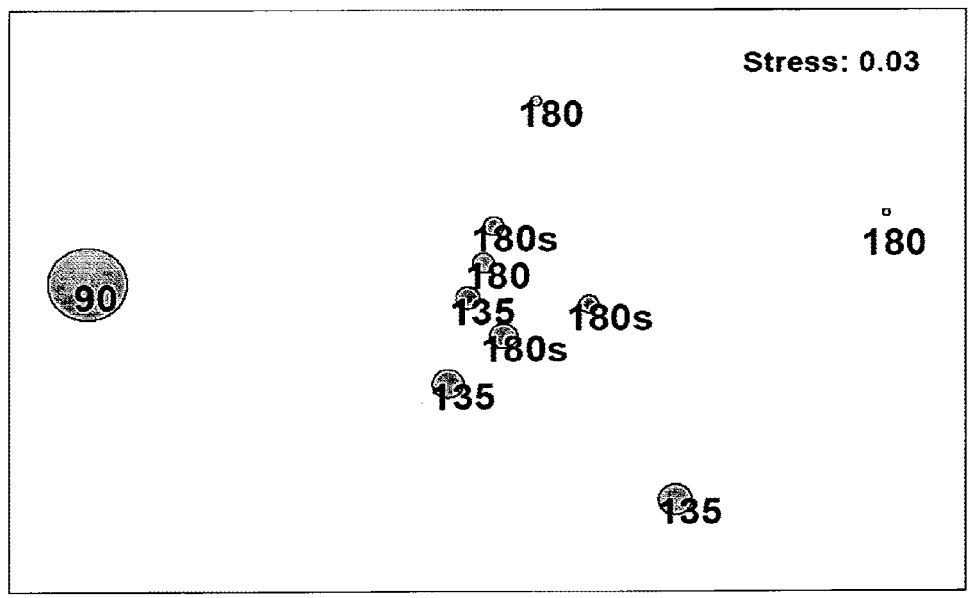
FIG. 4b. Multidimensional scaling analysis trace highlighting the dissimilarity between feral pig dose rate groups base on all pair wise coefficients as calculated with SIMPER analysis.

MDS analysis confirmed that some dose rates produced syndromes that were distinctly different to other feral pigs based on relative differences in clinical signs, time to death and Met Hb levels (see FIG. 4a). Extensive differentiation occurred with four individual feral pigs that received high or low doses. However, the majority of feral pigs showed little differentiation with one another, and these individuals all received higher doses. Generally, higher doses tended to coincide with more rapid times to death (see FIG. 4b). Global ANOSIM analysis showed that the difference between the groups of feral pigs receiving each dose was significant (R=0.296, P=0.02). It was clear that biggest dissimilarity between the feral pigs was between the group that received 90 mgkg$^{-1}$ and all other feral pigs when analysed with SIMPER. In other words, the average dissimilarity of all pair-wise coefficients between the 90 mgkg$^{-1}$ feral pig and all other dose rates was approximately 23% (see table 3). The feral pig that received 90 mgkg$^{-1}$ and died took longer to vomit, had a lower peak Met Hb value and took longer to die than the pigs which died after receiving the higher doses of SN (two feral pigs of this dose rate did not die and are not analysed in the MDS). Higher doses resulted in shorter time to clinical signs and death.

TABLE 3

The dissimilarity between feral pig dose rate groups base on all pairwise coefficients as calculated with SIMPER analysis.

| Pair-wise dose rate comparisons (mgkg$^{-1}$) | Dissimilarity |
|---|---|
| 180S vs. 180 | 10.44 |
| 180S vs. 135 | 7.82 |
| 180 vs. 135 | 13.08 |
| 90 vs. 135 | 22.38 |
| 90 vs. 180S | 20.55 |
| 90 vs. 180 | 25.76 |

The table demonstrates that the feral pig which received 90 mgkg$^{-1}$ was the most dissimilar to other feral pigs which received higher doses. The higher the dissimilarity figure, the more dissimilar are the pair-wise comparisons. The group represented by 108S received 180 mgkg$^{-1}$ with sodium carbonate.

Abnormalities were detected during post mortems in all animals which died following nitrite ingestion. The only consistent sign was dark or chocolate coloured blood and subsequent discolouration of organs and tissues which are well vascularised. Some animals (2) showed blood clots or frank blood in various areas, generally the thorax. One feral pig had profuse bleeding into the thorax and this may have been sufficiently extensive to contribute to death. This was a 44.8 kg male which died 47 minutes after gavage with a peak Met Hb level of 90.1%. Most feral pigs had pale coloured lungs with some petechial haemorrhages. One animal had a partial thickness stomach ulcer with some associated bleeding on the omentum. This may have been an existing pathological feature or it may have been associated with passage of the gavage tube. In contrast no abnormalities were detected in the 90 mgkg$^{-1}$ group or placebo feral pigs.

Bait Delivery Trial.
Palatability.

At low doses (135 mgkg$^{-1}$) where toxins was concentrated with honey in the middle of a bait (see Example 2), toxic baits were consumed readility. At 270 and 540 mgkg$^{-1}$ dose rates, two from three animals in each group consumed bait and toxin, with the third eating around the central honey/SN mass, and avoiding most of the toxin. At 135 mgkg$^{-1}$ when toxin was mixed with honey, in a 'clump' in wheat, two from three feral pigs refused any toxin, but ate the wheat around the toxic 'clump'. These two animals consumed the toxin readily when was dispersed throughout bait substrate (carrier material). For the other feral pigs receiving higher doses in wheat, the toxin was mixed throughout the wheat with a tablespoon of honey and all feral pigs consumed grain and toxin readily.

Deaths.

Most animals completely consumed all bait material within 10-30 minutes. Six animals received 135 $mgkg^{-1}$ of SN in bait substrate, the lowest effective gavage dose, but none died. Five animals consumed 270 $mgkg^{-1}$ of SN and one of these died. The final animal from this 270 mg/kg dose group only consumed part of it's toxin in a bait and did not die. All animals consuming 540 $mgkg^{-1}$ in either bait substrate died (4/4; 2 for each substrate). A fifth animal began showing clinical malaise whilst it was still consuming wheat and only ate 370 g of the 500 g of presented wheat but still died. Assuming even toxin dispersal throughout wheat it received approximately 400 $mgkg^{-1}$ of SN. The final animal from the high dose group consumed a partial dose (unknown amount) of SN in the bait and remained alive. The mean time to death for all dead animals was 141±49 min (S.D.). The mean time to death for the animals that received the full 540 $mgkg^{-1}$ dose was 122±49 min (S.D.). The mean time that clinical signs were displayed by all animals was 84±41 min. The mean time that clinical signs were displayed by the animals receiving the full 540 $mgkg^{-1}$ dose was 80±51 min. Animals that received sub-lethal doses recovered after approximately 600±187 min (10±3 hrs). The mean weight of poisoned feral pigs was 25±11 kg with four males and two females.

The claims defining the invention are as follows:

1. A method for selectively and humanely controlling a population of omnivorous feral animals, the method including the step of dispersing within the area of foraging of said omnivorous feral animals at least one bait comprising a solid or semi-solid carrier material and a nitrite salt, wherein the bait has an amount of nitrite salt which delivers at least 135 mg of nitrite per kg based on the weight of a feral animal in said population, the nitrite salt comprising at least 3% by weight of the total weight of the bait, and wherein the nitrite salt is present in the bait in an encapsulated form.

2. A method according to claim 1 wherein the nitrite salt is sodium nitrite.

3. A method according to claim 1 wherein the nitrite salt is in an amount which provides a lethal dose to a feral animal.

4. A method according to claim 1 wherein the amount of nitrite salt is between about 4 mg and about 30 g.

5. A method according to claim 4 wherein the amount of nitrite salt is between about 4 mg and about 15 g.

6. A method according to claim 1 wherein the nitrite salt is dispersed throughout the carrier material.

7. A method according to claim 6 wherein the carrier material comprises animal derived components.

8. A method according to claim 6 wherein the carrier material comprises fish meal.

9. A method according to claim 1 wherein the omnivorous feral animals are feral pigs.

10. A method according to claim 1 wherein the amount of nitrite salt is up to 15% or up to 25% by weight of the total weight of the bait.

11. A method according to claim 1 wherein death occurs within 2-3 hours after ingestion of the bait.

* * * * *